US009872967B2

(12) United States Patent
Sims et al.

(10) Patent No.: US 9,872,967 B2
(45) Date of Patent: Jan. 23, 2018

(54) COMPONENTS FOR MEDICAL CIRCUITS

(71) Applicant: Fisher & Paykel Healthcare Limited, East Tamaki, Auckland (NZ)

(72) Inventors: David John Sims, Auckland (NZ); Enrico Alvarez Garcia, Auckland (NZ); Peter Kenneth Graham, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 0 days.

(21) Appl. No.: 15/265,735

(22) Filed: Sep. 14, 2016

(65) Prior Publication Data

US 2017/0000967 A1 Jan. 5, 2017

Related U.S. Application Data

(63) Continuation of application No. 13/805,640, filed as application No. PCT/NZ2011/000111 on Jun. 16, 2011, now Pat. No. 9,468,733.

(Continued)

(51) Int. Cl.

*F24H 1/10* (2006.01)
*A61M 16/10* (2006.01)

(Continued)

(52) U.S. Cl.

CPC ...... *A61M 16/1095* (2014.02); *A61M 13/003* (2013.01); *A61M 13/006* (2014.02);

(Continued)

(58) Field of Classification Search

None

See application file for complete search history.

(56) References Cited

U.S. PATENT DOCUMENTS

| | | | | |
|---|---|---|---|---|
| 2,876,801 A * | 3/1959 | November | ............. | F16L 11/15 138/121 |
| 3,891,007 A * | 6/1975 | Kleykamp | ........... | B29C 47/126 138/121 |

(Continued)

FOREIGN PATENT DOCUMENTS

| | | |
|---|---|---|
| EP | 1832216 A1 | 9/2007 |
| JP | 2002 181257 | 6/2002 |

(Continued)

OTHER PUBLICATIONS

International Search Report; PCT/NZ2011/000111; dated Sep. 22, 2011; 5 pages.

(Continued)

*Primary Examiner* — Thor Campbell

(74) *Attorney, Agent, or Firm* — Knobbe, Martens, Olson & Bear LLP

(57) ABSTRACT

Condensation or "rain-out" is a problem in medical circuits and previous attempts to manage and/or prevent rain-out have resulted in relatively expensive and/or difficult to manufacture medical circuit components. The subject patent provides an improved medical circuit component for managing rain-out. In particular the component may be an improved breathing tube, or insufflation system limb comprising a helically corrugated tube preferably incorporating a heater wire.

17 Claims, 10 Drawing Sheets

1 2 7 2 7 9 17 18

Related U.S. Application Data

(60) Provisional application No. 61/357,333, filed on Jun. 22, 2010.

(51) Int. Cl.

| | |
|---|---|
| ***A61M 16/08*** | (2006.01) |
| ***A61M 16/16*** | (2006.01) |
| ***A61M 39/08*** | (2006.01) |
| ***B29D 23/18*** | (2006.01) |
| ***F16L 11/118*** | (2006.01) |
| ***F16L 53/00*** | (2006.01) |
| ***B29C 65/48*** | (2006.01) |
| ***B29C 65/56*** | (2006.01) |
| *A61M 13/00* | (2006.01) |
| *B29L 31/00* | (2006.01) |

(52) U.S. Cl.

CPC .... *A61M 16/0808* (2013.01); *A61M 16/0875* (2013.01); *A61M 16/16* (2013.01); *A61M 39/08* (2013.01); *B29C 65/4815* (2013.01); *B29C 65/4845* (2013.01); *B29C 65/562* (2013.01); *B29D 23/18* (2013.01); *F16L 11/118* (2013.01); *F16L 53/008* (2013.01); *A61M 13/00* (2013.01); *A61M 16/106* (2014.02); *A61M 16/161* (2014.02); *A61M 2207/00* (2013.01); *B29L 2031/7542* (2013.01); *Y10T 29/49002* (2015.01)

(56) References Cited

U.S. PATENT DOCUMENTS

| | | | | |
|---|---|---|---|---|
| 4,165,214 | A | 8/1979 | Lupke et al. | |
| 4,171,634 | A | 10/1979 | Perkins | |
| 4,342,612 | A * | 8/1982 | Lalikos | B29C 53/12 138/121 |
| 4,354,051 | A * | 10/1982 | Kutnyak | A47L 9/24 138/122 |
| 4,531,551 | A * | 7/1985 | Eichelberger | F16L 11/112 138/129 |
| 5,316,047 | A | 5/1994 | Kano | |
| 5,640,951 | A * | 6/1997 | Huddart | A61M 16/08 128/203.26 |
| 5,735,266 | A | 4/1998 | Smith | |
| 5,894,865 | A * | 4/1999 | Winter | B29C 63/18 138/121 |
| 6,078,730 | A * | 6/2000 | Huddart | A61M 16/08 219/536 |
| 6,219,490 | B1 * | 4/2001 | Gibertoni | A61M 16/08 138/33 |
| 6,269,813 | B1 | 8/2001 | Fitzgerald et al. | |
| 6,315,715 | B1 * | 11/2001 | Taylor | A61B 1/018 138/122 |
| 6,398,266 | B1 | 6/2002 | Crump | |
| 7,965,930 | B2 * | 6/2011 | Carlson | F16L 11/081 137/341 |
| 8,078,040 | B2 * | 12/2011 | Forrester | A61M 16/0875 392/481 |
| 8,563,864 | B2 * | 10/2013 | Carlson | F16L 11/081 137/341 |
| 8,657,270 | B2 * | 2/2014 | Takada | F16F 9/38 188/322.12 |
| 8,726,901 | B2 * | 5/2014 | Jassell | A61M 16/0875 128/200.24 |
| 9,468,733 | B2 | 10/2016 | Sims et al. | |
| 2009/0117302 | A1 | 5/2009 | Kanao | |
| 2013/0233318 | A1 * | 9/2013 | Graham | A61M 13/006 128/205.27 |
| 2014/0037276 | A1 * | 2/2014 | Carlson | F16L 11/1185 392/468 |

FOREIGN PATENT DOCUMENTS

| | | |
|---|---|---|
| WO | WO 1997/047348 A1 | 12/1997 |
| WO | WO 2009/022004 | 2/2009 |

OTHER PUBLICATIONS

Extended European Search Report; PCT/NZ2011/000111; dated Nov. 10, 2014; 6 pages.

Extended European Search Report in Application No. 16192989.8 dated Feb. 16, 2017 in 8 pages.

* cited by examiner

COMPONENTS FOR MEDICAL CIRCUITS

CROSS-REFERENCE TO RELATED APPLICATIONS

This application is a continuation of U.S. application Ser. No. 13/805,640, filed Mar. 8, 2013, which, is the U.S. National Phase application under 35 U.S.C. §371 of International Application No. PCT/NZ2011/000111, filed Jun. 16, 2011, which claims priority from U.S. Provisional Application No. 61/357,333, filed Jun. 22, 2010. The entirety of each of the foregoing applications is incorporated herein by reference.

BACKGROUND OF THE INVENTION

Field of the Invention

The present invention relates to components for medical circuits for conveying gases to and/or from a patient. In one particular aspect, the invention relates to conduits and in particular to heated breathing tubes for use in an inspiratory and/or expiratory limb of a breathing circuit. In another particular aspect the invention relates to a heated tube for a surgical insufflation system.

Description of the Related Art

In assisted breathing, particularly in, medical applications, gases having high levels of relative humidity are supplied and returned through flexible breathing tubes of a relatively restricted size typically between a range of approximately 10 mm to 25 mm diameter (covering both neonatal and adult applications). Such breathing tubes are ideally very light, resistant to kinking or pinching but also very flexible to ensure the greatest performance and level of comfort for the patient. The light weight of a breathing tube is very important to reduce any forces applied to the patient interface by the weight of the tube. Similarly, breathing tubes must be flexible and able to bend easily to achieve a high level of patient comfort, which in turn can improve patient compliance.

In medical applications, such as with assisted breathing, the gases inhaled by a patient are preferably delivered in a condition having humidity near saturation level and at close to body temperature (usually at a temperature between 33° C. and 37° C.). Condensation or rain-out can form on the inside surfaces of the breathing tubes as the high humidity breathing gases cool and/or come into contact with the relatively cooler breathing tube surface. Breathing gases exhaled by a patient are usually returned fully saturated and flow through an expiratory breathing tube. If the expired gas is allowed to cool as it passes along an expiratory breathing tube, condensation or rain-out may also occur.

Similarly, Continuous Positive Airway Pressure (CPAP) systems or positive pressure ventilation systems that provide patients suffering from obstructive sleep apnoea (OSA) with positive pressure breathing gases, also use breathing tubes for delivering (or removing) inspiratory (and/or expiratory) gases.

Condensate forming in a breathing tube (either inspiratory or expiratory) can be breathed or inhaled by a patient and may lead to coughing fits or other discomfort. Condensation within a breathing tube may also interfere with the performance of connected equipment and ancillary devices and/or various sensors.

Attempts have been made to reduce the adverse effects of condensation by either reducing the level of condensation, or providing collection points for draining condensed liquid from the tubing component. Reducing the condensation or rain-out has generally been achieved by maintaining or elevating the temperature above the dew point temperature of the breathing gas to reduce the formation of condensation. This temperature is typically maintained by a heater wire within the breathing tube, although the rain-out performance of these breathing tubes may not be complete due to a number of factors. Further, previous methods of heating the gases flow to reduce rain-out, typically result in heated tubing that has been expensive and/or difficult to manufacture. Particularly, in 'single use' applications such as typically found in hospital applications, the manufacturing cost of breathing tubes is critically important. It is highly desirable to even further reduce rainout, while preferably maintaining a low production cost, for example, by utilising a manufacturing method that is capable of high production speeds.

Similarly, during laparoscopic surgery with insufflation, it may also be desirable for the insufflation gas (commonly CO2) to be humidified before being passed into the abdominal cavity. This can help prevent 'drying out' of the patient's internal organs, and can decrease the amount of time needed for recovery from surgery. Even when dry insufflation gas is employed, the gas can become saturated as it picks up moisture from the patient's body cavity. The moisture in the gases tends to condense out onto the walls of the medical tubing or discharge limb of the insufflation system. The water vapour can also condense on other components of the insufflation system such as filters. Any vapour condensing on the filter and run-off along the limbs (inlet or exhaust) from moisture is highly undesirable. For example water which has condensed on the walls, can saturate the filter and cause it to become blocked. This potentially causes an increase in back pressure and hinders the ability of the system to clear smoke. Further, liquid water in the limbs can run into other connected equipment which is undesirable.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is an object of the present invention to provide a component and/or method of manufacturing a component that will at least go some way towards improving on the above or which will at least provide the public and the medical profession with a useful choice.

In a first aspect the invention consists in a component comprising: a helically corrugated tube wherein the corrugation profile comprises alternating outer crests and inner troughs; and a heater wire associated with said outer crests.

Preferably said tube has a substantially uniform wall thickness.

Preferably said tube has a maximum wall thickness not exceeding 3 times the minimum wall thickness.

Preferably said outer crests correspond to a location of maximum inner radius and maximum outer radius of said tube, and said inner troughs correspond to a location of minimum inner radius and minimum outer radius of said tube.

Preferably each said outer crest comprises a peak region, and the peak regions include local troughs comprising a small inward dip, and said heater wire associated with said outer crests is located within said dip.

Preferably said tube includes an outer sheath supported on said outer crests.

Preferably said outer sheath traps air between adjacent outer crests.

Preferably said outer sheath restrains said heater wire associated with said outer crests in said local trough.

Preferably said helically corrugated tube includes multiple helix corrugations.

Preferably said component further comprises a heater wire associated with said inner troughs.

Preferably said inner troughs has a different heating density than said heater wire associated with said outer crests.

Preferably said heater wire associated with said inner troughs has a lower heating density than said heater wire associated with said outer crests.

Preferably said helically corrugated tube has a varying helix pitch.

Preferably said helically corrugated tube has a continuously variable helix pitch.

Preferably said component is a conduit for use in at least part of the exhaust arm of an insufflation system.

Preferably said component is a breathing tube for use in a breathing circuit.

Preferably said component is a catheter mount or tube for connection to a patient interface.

Preferably said tube is flexible as defined by passing the test for increase in flow resistance with bending according to ISO 5367.

Preferably said tube is an extruded corrugated tube.

Preferably said tube is a breathing tube and is terminated by a first connector at an inlet and a second connector at an outlet, and wherein only one gases passageway is provided the length between said inlet connector and said outlet connector.

Preferably said tube is a corrugation transition region wherein said helical corrugations transition to a substantially annular corrugation in the vicinity of said first and second connector respectively.

In a further aspect the invention consists in a component comprising: a corrugated tube wherein the corrugation profile comprises alternating outer crests and inner troughs, and wherein said outer crests include a peak region, and the peak regions include local troughs comprising a small dip.

Preferably said tube has a substantially uniform wall thickness.

Preferably said tube has a maximum wall thickness not exceeding 3 times the minimum wall thickness.

Preferably said outer crests correspond to a location of maximum inner radius and maximum outer radius of said tube, and said inner troughs correspond to a location of minimum inner radius and minimum outer radius of said tube.

Preferably said tube includes an outer sheath supported on said outer crests.

Preferably said outer sheath traps air between adjacent outer crests and restrains said heater wire associated with said outer crests in said local trough.

Preferably said outer sheath further traps air in said local troughs.

Preferably said corrugated tube is a helically corrugated tube.

Preferably said helically corrugated tube includes multiple helix corrugations.

Preferably said helically corrugated tube has a variable helix pitch.

Preferably said tube includes a heater wire therein.

Preferably said component is a conduit for use in at least part of the exhaust arm of an insufflation system.

Preferably said component is a breathing tube for use in a breathing circuit.

Preferably said tube is flexible as defined by passing the test for increase in flow resistance with bending according to ISO 5367.

Preferably said tube is an extruded corrugated tube.

Preferably said tube is a breathing tube and is terminated by a first connector at an inlet and a second connector at an outlet, and wherein only one gases passageway is provided the length between said, inlet connector and said outlet connector.

Preferably each end of said tube is a corrugation transition region wherein said helical corrugations transition to a substantially annular corrugation in the vicinity of said first and second connector respectively.

In a further aspect the invention consists in a method of forming a component comprising: extruding a tube; passing said extruded tube into a corrugator and forming corrugations in said extruded tube having a corrugation profile comprising alternating outer crests and inner troughs; and wherein each said outer crest comprises a peak region, and the peak regions include local troughs comprising a small inward dip.

Preferably said corrugations are helical.

Preferably said method further comprises a step of winding at least one heater wire into said local trough.

Preferably said method further comprises applying an outer sheath over said component.

Preferably said step of applying said sheath comprises extruding a sheath over said component.

Preferably said extruded tube has a substantially uniform wall thickness at the time of corrugating.

Preferably said outer crests correspond to a location of maximum inner radius and maximum outer radius of said component, and said inner troughs correspond to a location of minimum inner radius and minimum outer radius of said component.

Preferably said helically corrugated component includes multiple helix corrugations.

Preferably said method further en vises a step of winding at least one heater wire into said inner troughs.

Preferably said heater wire associated with said inner troughs has a different heating density than said heater wire associated with said outer crests.

Preferably said heater wire associated with said inner troughs has a lower heating density than said heater wire associated with said outer crests.

Preferably said helically corrugated component has a varying helix pitch.

Preferably said helically corrugated component has a continuously variable helix pitch.

Preferably said tube is flexible as defined by passing the test for increase in flow resistance with bending according to ISO 5367.

Preferably said method further comprises terminating a first end with a first connector, and terminating a second end with a second connector, and wherein only one gases passageway is formed between said first connector and said second connector.

Preferably said step of forming said corrugations includes forming a transition region at each end of said component, and wherein said helical corrugations transition to a substantially annular corrugation in the vicinity of said first and second connector respectively.

In a further aspect the invention consists in components as herein described with reference to any one or more of the drawings except FIG. 8.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application and/or statements of, invention, individually or collectively, and any or all combinations of any two or more said parts, elements features or statements of invention, and where specific integers are mentioned herein which have known equivalents in the art to which this invention relates, such known equivalents are deemed to be incorporated herein as if individually set forth.

The invention consists in the foregoing and also envisages constructions of which the following gives examples only.

DETAILED DESCRIPTION OF THE PREFERRED EMBODIMENT

In the field of medical circuits, and in particular breathing circuits (including anaesthetic circuits), condensation or rain-out can be a particular problem where high humidity breathing gases come into contact with the walls of a component at a relatively lower temperature.

Figure 3:
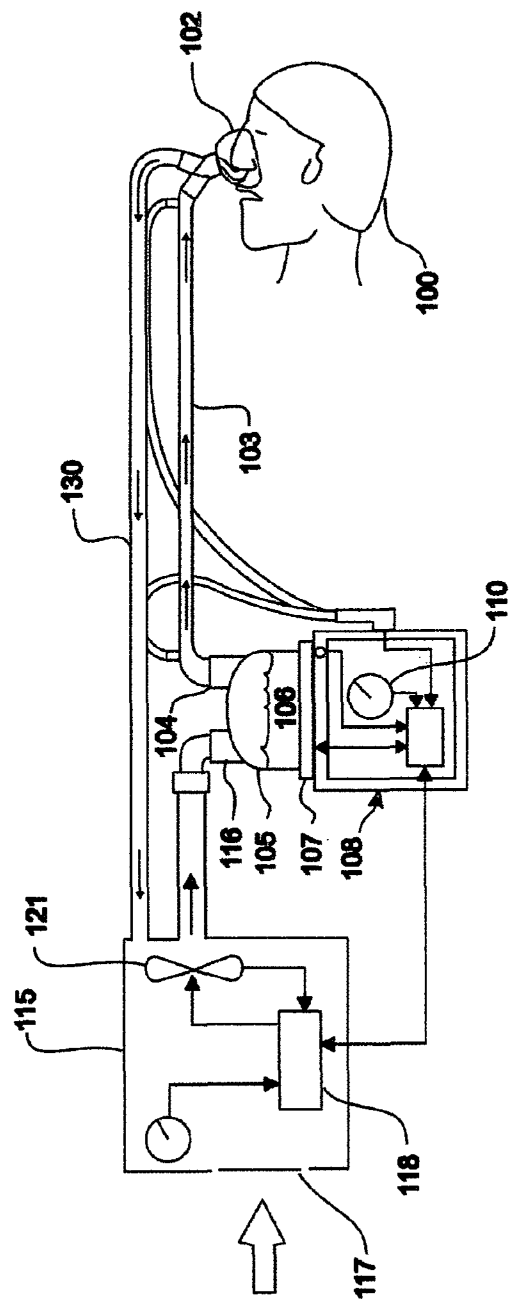
FIG. 3 is a schematic illustration of one type of breathing circuit in which a component according to the invention can be used.

With reference to FIG. 3 a humidified ventilation system is shown in which a patient 100 is receiving humidified and pressurised gases through a patient interface 102 connected to a humidified gases transportation pathway or inspiratory breathing tube 103. It should be understood that delivery systems could also be continuous, variable or bi-level positive airway pressure or numerous other forms of respiratory therapy. The inspiratory tube 103 is connected to the outlet 104 of a humidification chamber 105 which contains a volume of water 106. The inspiratory tube 103 may contain a heater or heater wires (not shown) which heat the walls of the tube to reduce condensation of humidified gases within the tube. The humidification chamber 105 is preferably formed from a plastics material and may have a highly heat conductive base (for example an aluminium base) which is in direct contact with a heater plate 107 of humidifier 108. The humidifier 108 is provided with control means or electronic controller which may comprise a microprocessor based controller executing computer software commands stored in associated memory.

In response to the user set humidity or temperature value input via dial 110, for example, and other inputs, the controller determines when (or to what level) to energise heater plate 107 to heat the water 106 within humidification chamber 105. As the volume of water within humidification chamber 105 is heated, water vapour begins to fill the volume of the chamber above the water's surface and is passed out of the humidification chamber outlet 104 with the flow of gases (for example air) provided from a gases supply means or ventilator/blower 115 which enters the chamber 105 through inlet 116. Exhaled gases from the patient's mouth are returned to the ventilator via a return expiratory breathing tube 130.

The ventilator 115 is provided with variable pressure regulating means or variable speed fan 121 which draws air or other gases through blower inlet 117. The speed of variable speed fan 121 is controlled by electronic controller 118. It will be appreciated the patient interface 102 could equally be a nasal mask, oral mask, oronasal mask, nasal prongs or full-face mask, etc.

However, there are also other competing requirements that should be satisfied by medical tubing in the field of the present invention. For example, it is preferable that breathing tubes for breathing circuits are: resistant to crushing; resistant to restrictions in flow when bent (increased resistance to flow <50% when bent around a 1 inch cylinder); resistant to kinking; resistant to changes in length/volume under internal pressure (compliance); resistant to leaking (<25 ml/min @ 6 kPa); have low flow resistance (increase in pressure @ max. rated flow <0.2 kPa); electrically safe i.e.: sparks in the tubing can be extremely dangerous, especially in oxygen-rich environments such as oxygen therapy.

International standard ISO 5367:2000(E) (Fourth ed., 2000-06-01) is one example of how some of these desirable parameters are measured and assessed, and the document is hereby incorporated into this specification in its entirety by reference. It is preferable that components of the invention meet or exceed some or all of these standards. In a most preferred embodiment components of the invention meet all of these standards.

Helically wound medical tube conduits including helical (or annular) reinforcing beads many times thicker than the tube wall thickness have been previously provided to improve crush resistance and to prevent blocking while maintaining a flexibility enabling the component to bend easily without kinking. However, these types of conduits are relatively difficult and slow to manufacture, resulting in higher costs. In many medical applications, breathing tube components are "single use" and are discarded regularly. Therefore, cost is a very important consideration for producing commercially viable products. Particularly for single use breathing tubes, a substantially uniform wall thickness extruded and corrugated tube is significantly cheaper and faster to manufacture and has therefore typically been preferred (for example breathing tubes formed from an extruded tubular parison). However, the rain-out performance has also typically been poorer. It is this type of extruded and corrugated tube, having dimensions and mechanical properties suitable for medical use, to which the present invention relates.

In this specification, terms "medical circuit" and "breathing circuit" are used to indicate the general field of the invention. It is to be understood that a "circuit" is intended to include open circuits, which do not form a complete closed circuit. For example, CPAP systems usually consist of a single inspiratory breathing tube between a blower and a patient interface. The term "breathing circuit" is intended to include such "open circuits". Similarly, the term "medical circuit" is intended to include both breathing circuits and insufflation circuits (which are also typically "open"). Similarly, the term "medical tubing" is intended to be read as flexible tubing suitable for use in the type of medical circuits described above connecting between components of a medical circuit and providing a gases pathway between components of a medical circuit.

Breathing Tubing

Medical tubing in the field of the present invention has a nominal bore size from approximately 10 mm to approximately 30 mm, and lengths ranging from approximately 300 mm to 2.5 m. In particular applications such as medical tubing to connect to an interface component the tubing may be significantly shorter (e.g. 50 mm to 300 mm). A catheter mount for example, may have a length of approximately 80 mm. A catheter mount is a single lumen tube which in use will carry both inspiratory and expiratory breathing gases to and from a patient respectively.

Figure 1:
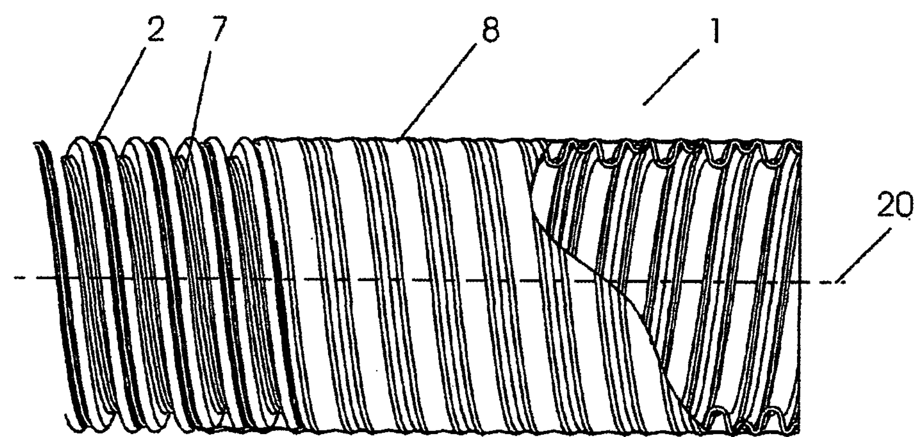
FIG. 1 is a partial cut-away side view of a medical tube component according to one embodiment of the invention for example a breathing tube or a limb of an insufflation system.
Figure 2:
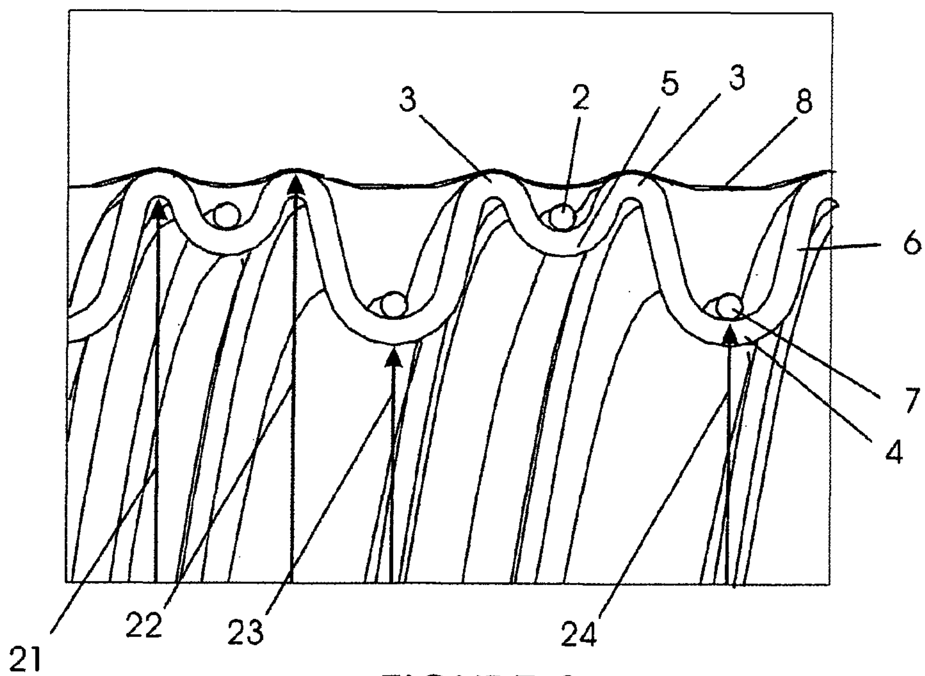
FIG. 2 is cross section view of the component of FIG. 1 showing a preferred corrugation profile.

With reference to FIGS. 1 and 2, an extruded breathing tube 1 with corrugations formed in a helical manner is shown. The corrugations comprise a series of alternating outer crests 3 and inner troughs 4 with respect to centre line 20. At the "peak" of each outer crest 3, is a local trough 5 comprising a small (with respect to the amplitude of the corrugations) inward dip in the peak. As a result, the "outer crest" 3 is intended to denote a region comprising the local trough 5 and the two local peaks adjacent either side. The outer crest 3, corresponds to a location of maximum inner radius 21 and maximum outer radius 22. The inner trough 4, corresponds to a location of minimum inner radius 23 and minimum outer radius 24.

An electrical heating wire 2 is placed in direct external contact to the tube 1 and wound along the local trough 5 associated with the outer crests 3 of the helical corrugations. As a result, the tube wall in the region of the peak of the outer crests 3 is heated directly. It has been found that a significant portion of heat lost occurs in the region of the outer crests 3 of a substantially uniform thickness corrugated tube, and therefore this has been found to be an effective location to apply heat in order to more efficiently reduce rain-out. Further, because the heater wire is associated with the exterior surface of the breathing tube, the gases flow through the conduit is not further disturbed by the presence of a heater wire in the flow path. The heater wire 2, is of a small diameter compared to the diameter of the tube.

In one embodiment, it is preferable that the heater wire 2 is formed in an electrical loop so that the electrical circuit starts and finishes at the same end of the breathing tube 1, which can be attached to a medical respiratory device that provides power to the heater wire circuit.

Therefore a second strand of heater wire 7, is preferably provided in the inner trough 4. The second strand of heater wire 7, may be part of the same heater wire 2 that has been looped back during manufacture. Alternatively, heater wire 7 may be a separate run of heater wire that is subsequently joined to heater wire 2 after winding.

Other arrangements of the heater wire are possible as illustrated by the following examples: two wires in tandem in each crest arranged in an electrical (series) loop; two wires in tandem in each trough arranged in an electrical (series connected) loop; two wires in tandem in each crest and two wires in tandem in each trough arranged in two separate electrical (series connected) loops; two wires in tandem in each crest and two wires in tandem in each trough arranged in a continuous electrical (series connected) loop in an arrangement with two complete return runs up and down the tube.

Attachment of electrical termination connectors and/or joining of the ends of the wires to create a return loop (or loops if multiples are desired) could be performed in a number of ways. These could include soldering, crimp connection, insulation displacement connection (IDC) and resistance welded joints. These connection methods can be implemented in various ways to achieve parallel, series or combinations of these methods depending on the desired result.

In another preferred embodiment, the heater wire 2 (associated with the outer crest 3) may also be selected with different electrical characteristics to apply more heat to the crest of the tube, when compared with heater wire 7 (associated with the inner trough 4). For example a higher heating density heater wire (e.g. higher resistance) may be used for the heater wire 2, than for the heater wire 7.

In another embodiment, the helical corrugations (either single or multiple helix arrangements described later) may have a varying pitch along the length of breathing tube. In this way because the heater wires 2, and 7 if present are wound with the corrugation profile, they will also have a varying pitch along the tube length. This results in varying heating density along the tube thereby allowing more (or less) heat to be applied to different regions of the tube as desired. For example a higher heating density may be desired at the chamber end where (typically) the highest rainout occurs (for an inspiratory breathing tube). This is because the gas is typically fully saturated at the chamber outlet. The inspiratory tube is heated to increase the gas temperature along the tube, thereby decreasing the relative humidity (and potential for rainout) of the gas as it flows towards the patient end. Similarly, in an expiratory breathing tube, an increased heating density may be desirable at the patient end of the tube and/or the machine end of the tube.

In a further preferred embodiment, a thin external sheath 8 is used to cover the tube and the heater wires 2, 7 to prevent them being dislodged and to further prevent heat loss. The sheath 8 provides an insulating barrier by trapping air in the space between adjacent outer crests 3 and the outer wall of the tube (in the region of the inner troughs 4). The crest region 3 including local trough 5, also provides improved insulation in the crest region where air is trapped in the space (if any) between the sheath 8 and the local trough 5, because the conduction pathway where the sheath is in contact with the crests is reduced.

Figure 5:
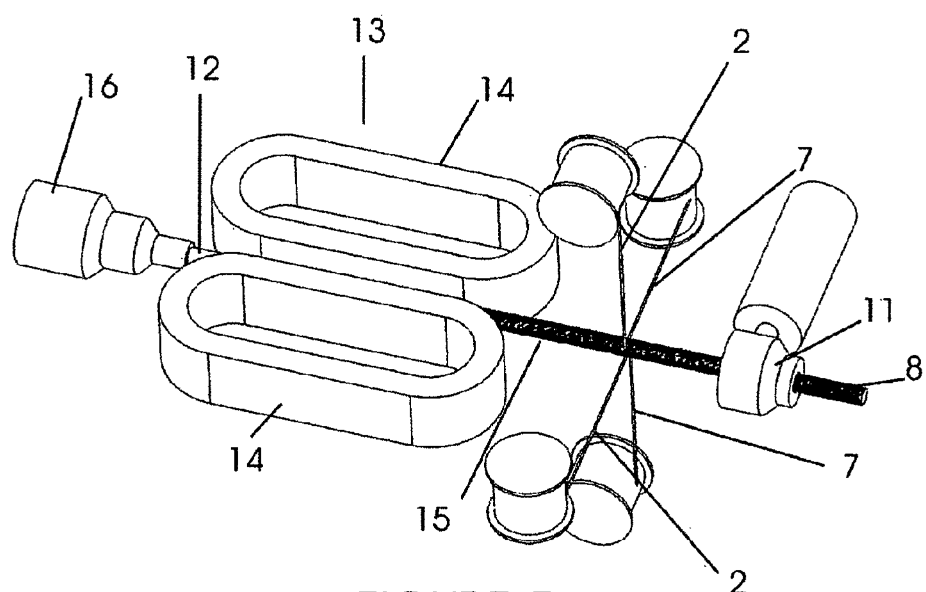
FIG. 5 is a schematic illustration of a preferred forming method for medical tubing.

The sheath 8 may or may not contact and hold the heater wire in place. The sheath can be formed by for example; spiral wrapping a cling tape over the outside or by feeding the mandrel through a cross-head die 11 and extruding a thin flexible plastic sheath 8 over the top as shown in FIG. 5. The sheath has the added benefit of improving compliance, (i.e.: reducing longitudinal stretch), pull strength, resistance to flow with bending and crush resistance, although it is important that the overall product still remains flexible to ensure adequate patient comfort etc. It will be appreciated that if an extruded sheath is employed, it may be able to be bonded securely to the tube during the extrusion process. This may have benefits in improving the torsional resistance of the tube and limit the effects of a torsional "worming" action that can occur with a spiral formed tube when experiencing a pulsing pressure as typically experienced in a breathing circuit.

The sheath 8, may be of the same material (or same base material) as the breathing tube, particularly for embodiments where bonding between the sheath and tube or between the sheath and breathing tube end connectors is desired. Bonding, if my, may be from residual heat in the sheath as it is formed over the breathing tube, and/or auxiliary heating/welding processes may be employed. Alternatively, the sheath 8 may be of a different material, and a bonding agent may be applied if bonding is desired.

In a further alternative embodiment, the tube of FIG. 2 including outer sheath 8 may be provided without any heater wires. In this embodiment improved insulation results from the crest region where air is trapped in the space between the sheath 8 and the local trough 5. Further, the helical corrugations also improve mixing of the flow in the tube and reduce rainout. It has been found that the performance of this unheated embodiment is superior to an unheated sheathed conduit of conventional annular corrugation form such as illustrated in FIG. 9 (sheath not shown). It has also been found that the performance of an internally heated embodiment of the conduit utilising a corrugation form with a dip in the crest and an external sheath, is superior to an internally heated sheathed conduit of conventional corrugation form such as illustrated in FIG. 9 (sheath not shown).

It will be appreciated that other reinforcing processes may also be used to supplement the tube in order to improve its performance characteristics still further (such as compliance, pull strength, resistance to flow with bending and crush resistance). Those processes may or may not be integrated with the tube forming process.

In a further embodiment, the helical corrugations may be formed in a multiple start arrangement comprising a plurality of helical corrugations (i.e. a double helix incorporating two crests and two troughs per pitch etc.). With this configuration, shown in FIG. 5, spiral winding of more than one pair of heater wires 2, 7 can be achieved per revolution. For example:

a double helix with heater wire in the crests (only) arranged in an electrical (series) loop a double helix with heater wire in the troughs (only) arranged in an electrical (series connected) loop a double helix with a wire in each crest and a wire in each trough (two of each per pitch) arranged in two separate electrical (series connected) loops. This can be achieved by creating two "crest to trough" linked circuits or a "crest to crest" and a "trough to trough" linked circuit. In the case of the latter arrangement, separate electrical control of the heating of crests and troughs would be possible.

a double helix with a wire in each crest and a wire in each trough (two of each per pitch) arranged in a single (series connected) electrical loop. This can be achieved by connecting appropriate adjacent crest and trough wire ends to form an arrangement with two return runs.

a double helix with a wire in each crest and a wire in each trough (two of each per pitch) arranged in a parallel-series connected electrical loop. This can be achieved by connecting adjacent crest and trough wire ends into two pairs at the chamber end with appropriate terminations such as pins to accept a plug to allow subsequent connection to the power supply. This would form one end of two separate parallel connected pairs. At the patient end, all the wire ends can be linked together in a circumferential loop. This then links the patient ends of the parallel pairs (completing the two parallel loops) and also connects the ends of the two parallel pairs in series to complete the circuit return run.

a double helix with two wires in tandem in each crest and two wires in tandem in each trough. This would allow multiple combinations of separate or linked circuits connected in series, parallel, parallel-series or series-parallel to provide various winding and termination options for production or to achieve heating or control benefits.

Other multiples of helixes per pitch with associated pairs of wires (including tandem wires in each groove) can be employed in a similar fashion with more complex connection options.

Attachment of electrical termination connectors and/or joining of the ends of the wires to create (a) return loop(s) could be performed in a number of ways as described earlier.

The multi-helix arrangement will also reduce the time required to wind the heater wires during manufacture, since the maximum rpm of the winding equipment is limited by balance issues, wire feed speed and safety. Winding multiple wires simultaneously, allows more wire to be wound at any given winding speed. A further benefit arises by increasing the number of breathing tubes (continuous production length) that can be produced before changing reels of heater wire. These benefits directly enhance the throughput of each production line.

The winding process can be performed in a number of ways depending on the desired connection devices and tube handling method(s).

Reverse-Looped Spiral Heating Filament.

In this embodiment, the wire(s) is (are) wound onto the tube in one direction, and then looped around (for example on the patient end of the tube) before winding back along the tube to the starting point to complete the loop. Tube handling for this method is best performed by cutting the continuous output from the corrugator into individual tubes, loading them onto mandrels and transferring the mandrels onto a winding machine. The winding machine may have several stations that rotate the mandrels and spiral the wire onto the tube, reversing at the end before winding back along the tube to complete the circuit. The loose ends at the chamber end could be retained, for example with a clip system or by hot melt glue or similar adhesive. Once the wire winding is complete, the tube can be sheathed (if desired) to cover and retain the wire.

Pre-Looped Spiral Heating Filament.

In this embodiment, the wire(s) is (are) pre-loaded onto an accumulator system and doubled over complete with a loop in the middle ready for transfer onto the tube. The wire loop(s) is (are) wound onto the accumulator drum in one direction, then back to the other end for example. The winding onto the tube is therefore performed in one direction only. This can either be done on a separate mandrel system as per the previous option or it could be performed in-line direct off the corrugator. The advantages of spiralling on-line eliminate the mandrels and associated handling equipment. Once wire is loaded, the tubing can be routed through a cross-head die for sheathing (if desired) as shown in FIG. 5 for example.

Paired Heating Filaments with Joints at One End (e.g. at the Patient End)

In this embodiment, corrugated joined tubes pass directly from the corrugator through a joiner/winder assembly. This joins the ends of pairs of wire strands together, then positions them over the corrugation spiral and may require further securing with for example, hot melt glue or UV curing adhesive, or a retaining clip. The winder head then rotates around the tube and applies paired runs of wire from separate spools at the same time. The number of wire pairs to suit the number of helixes per pitch and the desired wire arrangements. The over-sheath (if desired) is subsequently fitted, and then the tubes are separated at the cuffs. Finally, the cuff fittings and end terminations are fitted.

In this alternative embodiment, the pairs of wires could be continuously spiraled around the tube and joined with a crimp connector without first cutting the wires. The over-sheath is subsequently fitted, and then the wires are cut after the tubes are separated at the cuffs. Finally, the cuff fittings and end terminations are inserted.

Paired Heating Filaments Continuously Wound On-Line

In this embodiment, corrugated joined tubes pass directly from the corrugator through a winder assembly. The winder heads rotate around the tube and apply paired runs of wire from separate spools at the same time. The number of wire pairs to suit the number of helixes per pitch and the desired wire arrangements. The wires may require securing with for example hot melt glue or UV curing adhesive or a retaining clip at the ends of the tubing to prevent unraveling once the tubes are separated. The over-sheath is subsequently fitted (if required), the tubes are separated and then the wires terminated via an appropriate method in a final assembly operation. This allows for a continuous winding process with the rotational speed of the winding heads largely constant. Feed rate can vary as required to suit the pitch of the grooves at the section of the tube being wound.

Figure 8:
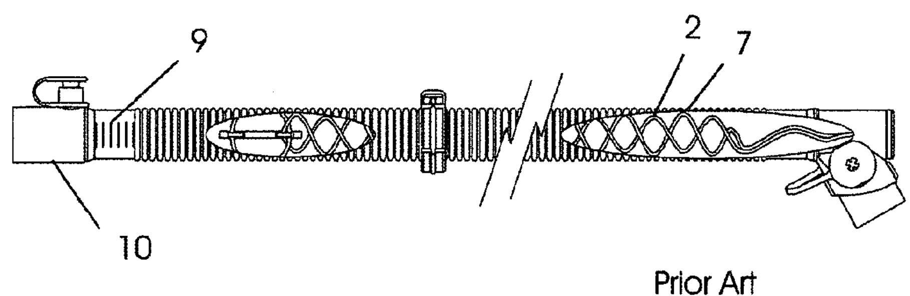
FIG. 8 is a side view of a prior art annular corrugated conduit with internal spiral heater wire.
Figure 9A:
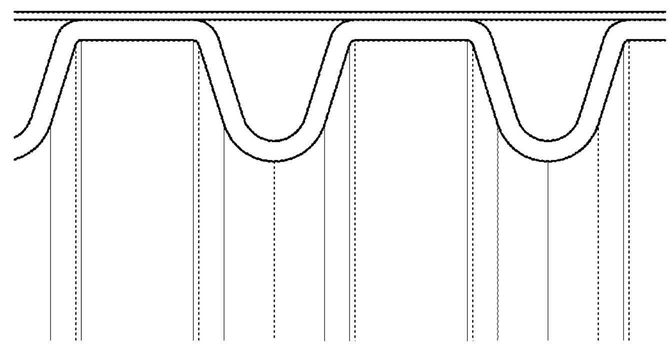
FIGS. 9A-9F illustrate a plurality of different embodiments of breathing tube configurations. As is described in the "Calculated Condensate Build-up for Non-heated Tube Options" Table, the condensate build-up is provided for each of the non-heated tube options of FIGS. 9A-9F.
Figure 9B:
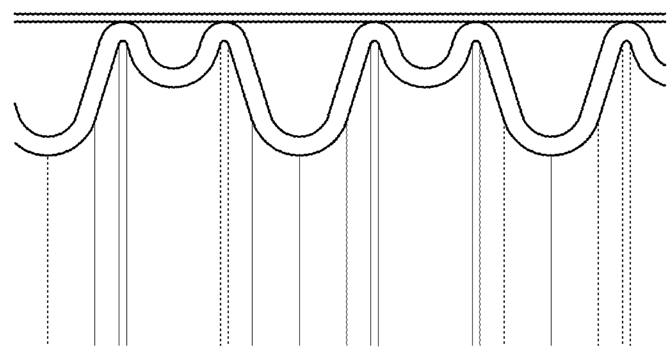
Figure 9C:
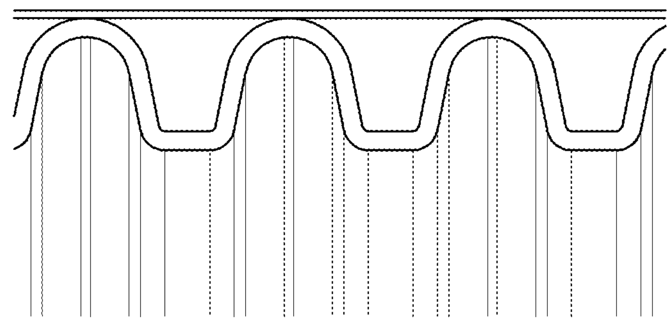
Figure 9D:
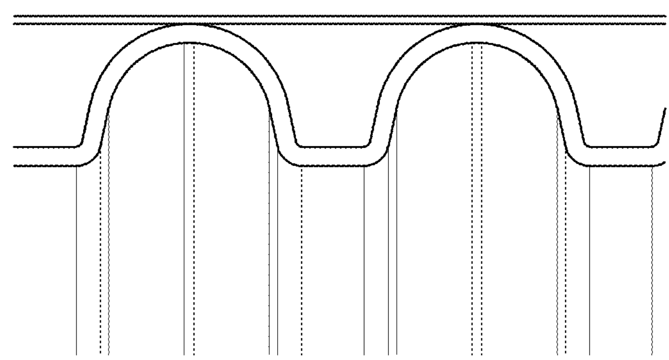
Figure 9E:
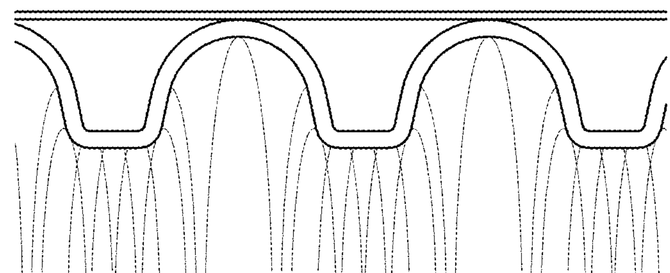
Figure 9F:
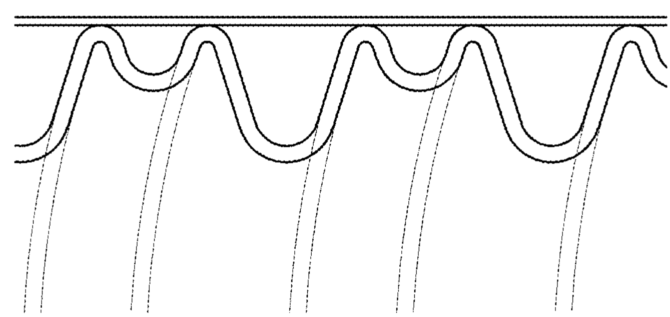
Figure 9G:
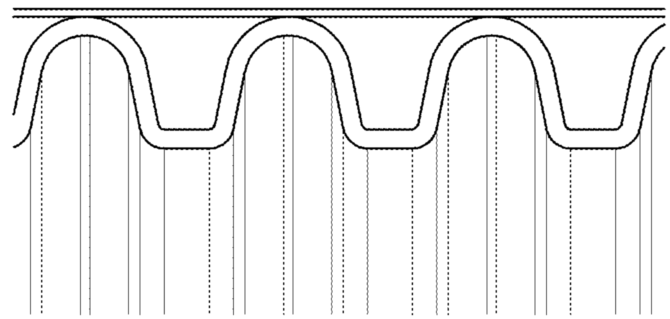
FIGS. 9G-9I illustrate a plurality of different embodiments of breathing tube configurations. As is described in the "Calculated Condensate Build-up for Heated Tube Options" Table, the condensate build-up is provided for each of the heated tube options of FIGS. 9G-9I.
Figure 9H:
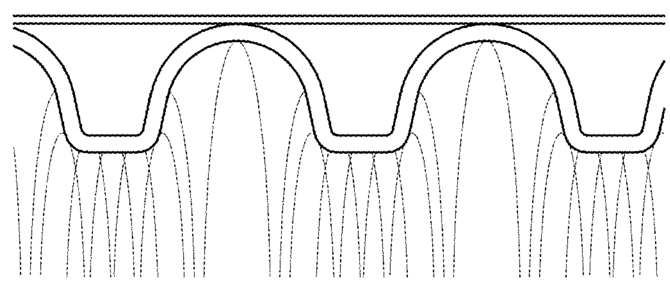
Figure 9I:
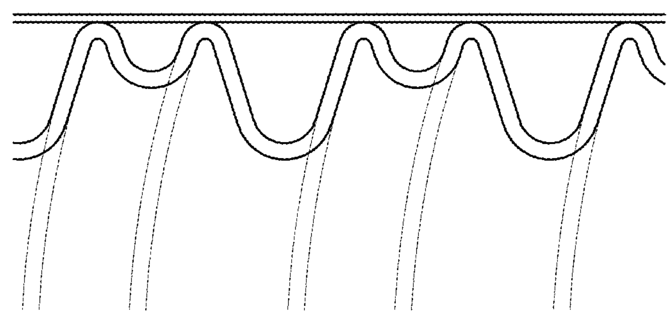

Testing has demonstrated the performance improvements of the present medical tubing, compared to prior art breathing tubes comprising an annular corrugated tube having an internal spiral heater wire such as shown in FIG. 8 for example.

In further embodiments it is envisaged that the helical corrugations may also carry conductor(s) for sensors located somewhere along the tube i.e. temperature, humidity, flow or pressure sensors etc. These conductors may share a local trough 5 (and/or inner trough 4) in common with a heating wire or may be formed as an additional helix run with a separate local trough 5 (and/or inner trough 4). This would remove the need for a separate loose cable thereby reducing complexity of setup and associated clutter around the patient. Alternatively, one or more heater wires may be used to also carry signal from a sensor or transducer.

With reference to FIG. 5, the preferred process used to make medical tubing involves extruding a molten tubular profile 12 into a corrugator machine 13 utilising an endless chain of mould blocks 14 to form a flexible helically corrugated tube 15. An extruder 16 such as a Welex extruder equipped with a 30-40 mm diameter screw and typically a 12-16 mm annular die head with gap of 0.5-1.0 mm has been found to be suitable for producing low cost tubes quickly. Similar extrusion machines are provided by American Kuhne (Germany), AXON AB Plastics Machinery (Sweden), AMUT (Italy), Battenfeld (Germany and China).

A corrugator such as those manufactured and supplied by Unicor® (Hassfurt, Germany) has been found to be suitable for the corrugation step. Similar machines are provided by OLMAS (Carate Brianza, Italy), Qingdao HUASU Machinery Fabricate Co., Ltd (Qingdao Jiaozhou City, P.R. China), or Top Industry (Chengdu) Co., Ltd. (Chengdu, P.R. of China).

During manufacture, the molten tube 12 is passed between a series of rotating moulds/blocks 14 on the corrugator after exiting the extruder die head 16 and is formed into a corrugated tube such as that illustrated in FIGS. 1 & 2 for example. The molten tube is formed by vacuum applied to the outside of the tube via slots and channels through the blocks and/or pressure applied internally to the tube via an air channel through the centre of the extruder die core pin. If internal pressure is applied, a specially shaped long internal rod extending from the die core pin and fitting closely with the inside of the corrugations may be required to prevent air pressure escaping endways along the tube.

The tube 1 has a wall 6 that is preferably between approximately 0.3-1 mm thick for a breathing tube of typical dimensions (i.e. between approximately 10 mm and 30 mm diameter for neonatal and adult applications respectively and approximately 1-2 meters in length).

With reference to FIG. 8, a typical prior art medical conduit includes a plain cuff region 9 for connection to an end connector fitting 10. Similarly, the end connector fitting of the present tube is preferably of a standard type (for example, the end connector may be plastic and incorporate a medical taper) according to the intended use of the medical tubing and is preferably permanently fixed. Fixing methods may include friction fit, adhesive bonding, over moulding, or thermal or ultrasonic welding etc.

One advantage of the preferred type of tube manufacture described above with reference to FIG. 5, is that some of the mould blocks 14 can include end cuff features that are formed at the same time as the tubing. Manufacture speeds can be significantly increased by the reduction in complexity and elimination of secondary manufacturing processes. While this method is an improvement over separate cuff forming processes, a disadvantage of the prior art plain cuff is that the corrugator must slow down to allow the wall thickness of the tube in this area to increase (the extruder continues at the same speed). The cuff thickness is increased to achieve added hoop strength and sealing properties with the cuff end connector or adaptor fitting. Further, the heat of the molten plastic in this thicker region is difficult to remove during the limited contact time with the corrugator blocks and this can become an important limiting factor on the maximum running speed of the tube production line.

Figure 6:
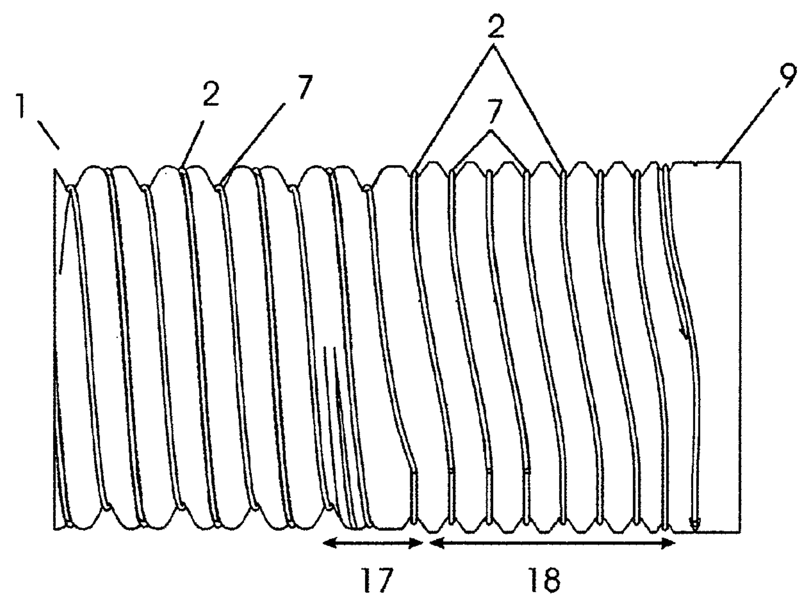
FIG. 6 is a side view of a medical conduit showing one preferred corrugation transition region and channels formed in the annular sealing rings to allow the heater wires to step over each annular ring as they transition along the cuff region adjacent an end cuff portion (with outer sheath not shown).
Figure 7:
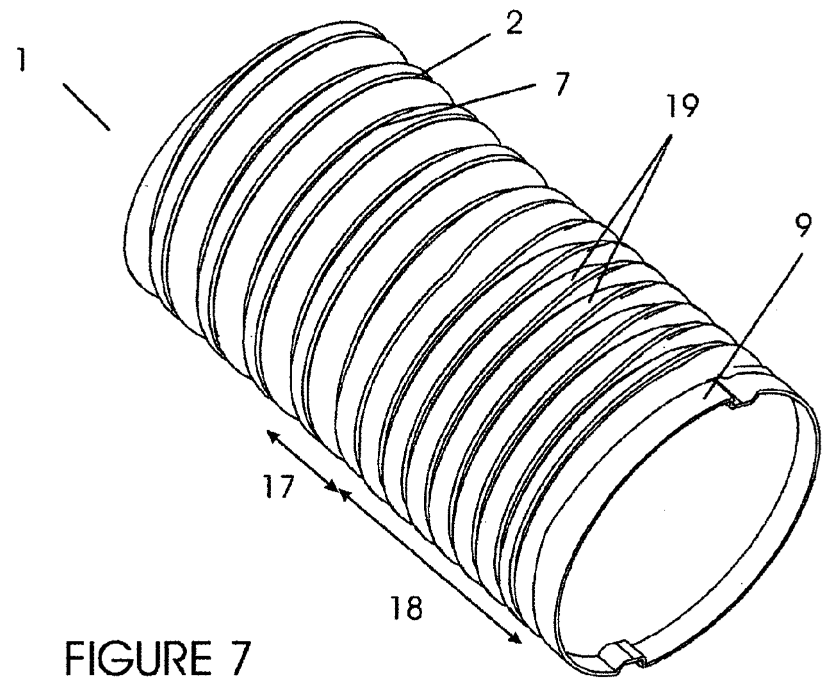
FIG. 7 is a schematic view of a medical conduit showing the preferred corrugation transition region of FIG. 6.

With particular reference to FIGS. 6 & 7, the end cuff region of the present medical tube (17+18+9) is formed at the same time as the spiral/helical corrugations, and is configured to receive an end connector adapter fitting 10 (not shown). Also, to facilitate the connection and wire routing between the spiral corrugation region of tube 1 (i.e. left hand side of conduit shown), and the annular cuff corrugation sealing region 18, a transition region 17 may be provided. The region 17 transitions from the helical corrugation profile to a mostly annular corrugation profile adjacent the open cuff end 9. The annular region 18 provides a better seal between the exterior surface of the cuff adaptor 10 (not shown) because the inner surface of each annular corrugation contacts the end connector 10 in independently sealed rings. Also the geometry of the corrugations provides a useful increase in sealing pressure and reduces the effects of diametric tolerances because the flexing of the angled walls transfers the hoop loads from the rings over a wider range of interference fits. This also allows the cuff region (17, 18, 9) to be a similar thickness to the helical corrugations of the conduit, thereby eliminating one of the reasons for the lower production speed attributed to cuff regions in prior art conduits, increasing productivity and reducing manufacturing costs of this conduit.

The annular region 18 also reduces heat loss from the cuff region by improving insulation due to the trapped air between the corrugations, the adaptor 10 (not shown) and the outer sheath. With particular reference to FIG. 7, the annular corrugation region 18 has angled channels 19 formed in, or on, the annular sealing rings in at least one row to allow the wires to step over each annular ring as they transition along the cuff region 18 towards the end of the cuff 9. In this way the wires can be routed to the end of the tube so that termination connections can be made without penetrating the sheath (not shown).

Preferred materials for manufacturing the medical tubing of the invention are Linear Low Density Polyethylene (LLDPE), Low Density Polyethylene (LDPE), Polypropylene (PP), Polyolefin Plastomer (POP), Ethylene Vinyl Acetate (EVA) or blends of these materials. Plasticised PVC may also be a suitable material, but it is not as well accepted for environmental reasons.

Preferred materials for the heater wires are copper, aluminium or a PTC (positive temperature coefficient) type material. Aluminium is not as conductive as copper, but may be an economical choice even though the wire diameter is larger for the same resistance. While the applied circuit voltage is intrinsically safe (less than 50V), for corrosion resistance and best electrical safety in the event of the tube or sheath being damaged, the wire will ideally be self insulated, either by enamel coating or anodising in the case of aluminium. Alternatively an extruded plastic sheath can be fitted, to insulate the wires from the surroundings.

Test Results

A computer model was used to demonstrate the effectiveness of the conduit constructions of the present invention. Different corrugation forms of an inspiratory tube were modeled in Ansys CFX to compare expected condensate accumulation during extreme use conditions of 18° C. ambient temperature and high convective heat loss. At the inlet, a continuous mass flow rate of 30 liters per minute at 37° C. was used and a convective heat transfer coefficient, h, of 50 W/m2° K. at 18° C. was applied on the surface of the insulation sheath to account for heat loss to the environment. This assumption approximately simulates a condition where cold air is blown over the surface of the tube from an air-conditioning vent for example.

The model analysis obtained the temperature at the outlet (Td) which approximates dew point when air is assumed to be at saturation. The absolute humidity, AH, was then calculated from the dew point and reference temperatures from the following equations:

$$P_v = P_{v,sat} \times \exp\left(\frac{H_v}{R_w} \times \left(\frac{1}{T_{ref}} - \frac{1}{T_d}\right)\right) \quad (1)$$

$$AH = \frac{P_v}{T \times R_w} \quad (2)$$

where

Pv=vapor pressure

Pv,sat=reference saturation, vapor pressure

Hv=latent heat of vaporization

Rw=gas constant for water vapor

Tref=reference temperature

Td=dew point temperature

The following tables summarize the boundary condition assumptions and the material properties used in the model of a typical adult sized breathing tube.

Model Boundary Condition Asumptions

| Parameter | Value |
|---|---|
| Inlet Air Temperature, $T_{air\_inlet}$ | 37° C. |
| Humidifier Air Flow Rate | 30 L/min |
| Reference Pressure, $P_{ref}$ | 1 atm |
| Power | 37 W |
| Ambient Temperature (outside tube), $T_{ambient}$ | 18° C. |
| Convective Heat Transfer Coefficient (outside tube), h | 50 $W/m^2$-°K |

Material Properties

| Component | Thermal conductivity, W/m-° K | Remarks |
|---|---|---|
| Tube | 0.3 | LLDPE Typical |
| Sheath | 0.3 | LLDPE Typical |
| Gap | 0.0261 | Air |
| Inspired Air | 0.0533 | Air (compensated for humidity) |

The resulting calculated condensate build-up for different breathing tube configurations are presented in the tables below. Predicted results were calculated for non-heated embodiments and heated embodiments of the present invention as described.

Calculated Condensate Build-up for Non-heated Tube Options

| Description of tube and corrugation form | | Dew Point (° C.) | Condensate Wt. (grams in 8 hrs) |
|---|---|---|---|
| External sheath + Flat Crest Annular Corrugation (pitch = 4.52 mm) | See FIG. 9A | 30.6 | 190.1 |
| External sheath + Annular Corrugation With Dip in Crest (pitch = 4.52 mm) | See FIG. 9B | 31.5 | 165.9 |
| External sheath + Rounded Annular Corrugation (pitch = 3.53 mm) | See FIG. 9C | 30.8 | 184.1 |
| External sheath + Rounded Annular Corrugation (pitch = 4.52 mm) | See FIG. 9D | 30.8 | 184.8 |
| External sheath + Spiral Corrugation (pitch = 4.52 mm) | See FIG. 9E | 32.1 | 150.0 |
| External sheath + Spiral Corrugation With Dip in Crest (pitch = 4.52 mm) | See FIG. 9F | 32.6 | 134.9 |

The results above show that the expected condensation volume is relatively insensitive to the pitch of the annular corrugations. Comparing the rounded annular corrugation tube with the dip in crest tube shows a significant reduction in condensation formation (approximately 10% improvement). Similarly, comparing the rounded annular corrugation with the spiral corrugation configuration shows a significant improvement (approximately 19%). The results further demonstrate that the performance enhancements from the spiral corrugation and the dip in the crest are cumulative and result in a tube having significantly superior condensation performance.

Calculated Condensate Build-up for Heated Tube Options

| Description of tube and corrugation form | | Power (W) | Location of Heater Wire | Condensate Wt. (grams in 16 hrs) |
|---|---|---|---|---|
| External sheath + Annular rounded Corrugation (pitch = 3.53 mm) | See FIG. 9G | 37 | Internal | 123.2 |
| External sheath + Spiral Corrugation (pitch = 4.52 mm) | See FIG. 9H | 37 | Trough | 43.7 |
| | | | Internal | 114.0 |
| External sheath + Spiral Corrugation With Dip in Crest (pitch = 4.52 mm) | See FIG. 9I | 37 | Trough | 23.5 |
| | | | Dip in Crest | 17.3 |
| | | | Crest + Trough | 15.8 |
| | | | Internal | 106.6 |

The results for the heated tube above show that heating the tube wall directly results in significantly better condensate performance compared to a tube with an internal heating wire of the same power. In particular, comparing the spiral corrugation with a heater wire in the trough with the same tube construction having an internal heater shows an enormous improvement in condensation performance (i.e. 106.6 g vs. 23.5 g (approximately 78% improvement)).

Similarly, locating the heater wire in a dip in the crest resulted in 17.3 g of condensate. This demonstrates a significant advantage in positioning the heater wire in a dip in the crest of the spiral corrugations.

The results further show that the best performing configuration is a tube having a spiral corrugation including a dip in, the crest and wherein a heater wire is located in both the dip in the crest and in the troughs. The cumulative effect of direct wall heating and the elimination of stagnant gas flow by the spiral corrugations results in, only 15.8 g of condensate (compared to 184 g of condensate for an unheated tube with rounded annular corrugations).

All of the configurations shown in the tables include an external insulation sheath around the corrugated tubes. The spiral corrugation form contributes significantly to the reduction in condensation formation compared to annular corrugated tubes by promoting good mixing of the gases in the corrugation peak areas. This effect is significant in both heated and unheated configurations.

The term "substantially uniform" wall thickness corrugated tube, is intended to mean a tube having a corrugation profile wherein the location of an outer peak, for example, comprises the maximum outside radius of the tube while also comprising the maximum inner radius of the tube. In addition, the location of an inner trough, for example, comprises the minimum inner and outer radius of the tube. This type of tube is typically formed from a substantially uniform thickness extrusion that is subsequently corrugated. It will be appreciated that the subsequently formed corrugations may vary the measured wall thickness of the outer peak regions vs. inner the trough regions of the finished tube. The ratio of minimum to maximum actual wall thickness may vary as much as 1:1.5-3.0 for example, but still be defined as "substantially uniform".

Component of an Insufflation System

Laparoscopic surgery, also called minimally invasive surgery (MIS), or keyhole surgery, is a modern surgical technique in which operations in the abdomen are performed through small incisions (usually 0.5-1.5 cm) as compared to larger incisions needed in traditional surgical procedures. Laparoscopic surgery includes operations within the abdominal or pelvic cavities.

In abdominal surgery, for example, the abdomen is usually insufflated with carbon dioxide gas to create a working and viewing space. The gas used is generally $CO_2$ which is common to the human body and can be absorbed by tissue and removed by the respiratory system. It is also non-flammable, which is important because electrosurgical devices are commonly used in laparoscopic procedures. The use of these devices tends to create surgical smoke in the working space due to burning of tissue. Smoke evacuation systems which use a discharge arm or limb are commonly used to remove the smoke from the surgical site, so that a surgeon can see what he or she is doing, and so that this potentially harmful material does not remain within the body cavity post-surgery.

A typical smoke evacuation system generally includes a trocar and a cannula at the end to aid insertion into the operative site. The smoke exits the insufflated abdominal area through the discharge limb The discharge limb may be attached to the end of a laparoscopic instrument so as to provide evacuation close to the site where electrocautery takes place. Usually, the gases and smoke from the body cavity are filtered through a filter to remove particulate matter before they are vented to atmosphere.

It has been common practice in laparoscopic surgery to use dry gases. However, it is also desirable for the $CO_2$ or other insufflation gas to be humidified before they are passed into the abdominal cavity. This can help prevent 'drying out' of the patient's internal organs, and can decrease the amount of time needed for recovery from surgery.

Figure 4:
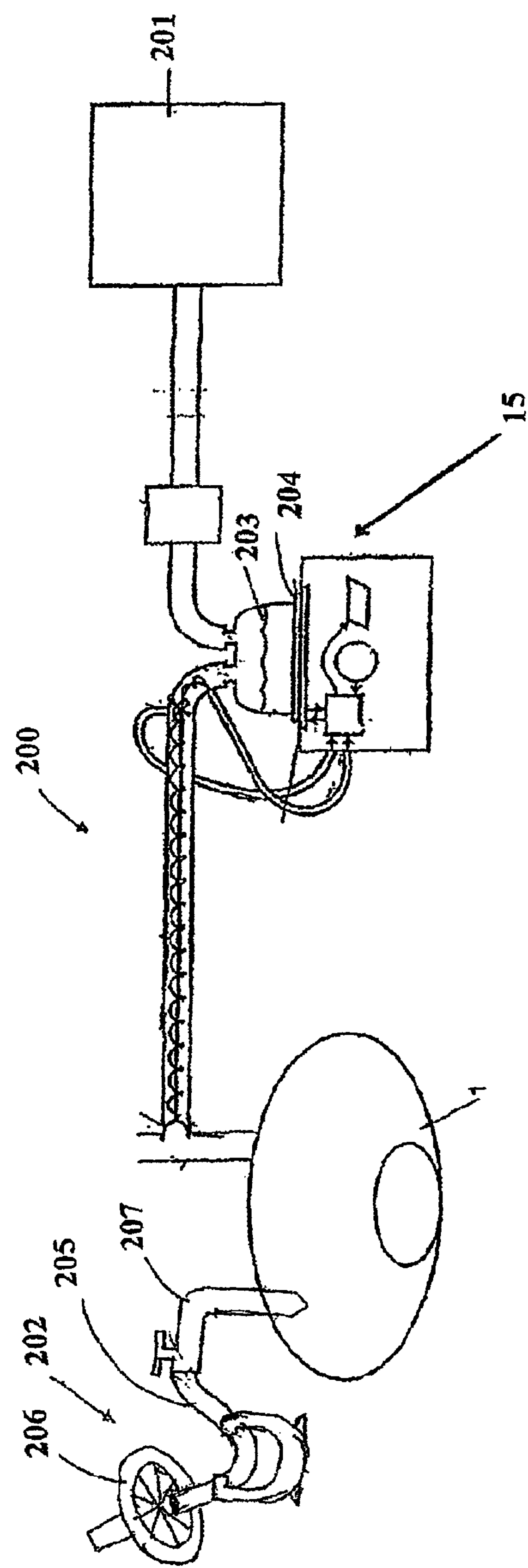
FIG. 4 is a schematic illustration of a patient and a humidified insufflation system showing the inlet and exhaust limbs.

FIG. 4 shows a typical insufflation system 200 such as might be used with the present invention. The insufflation system 200 includes an insufflator 201 that produces a stream of humidified insufflation gases at a pressure above atmospheric for delivery into the patient's abdominal or peritoneal cavity. The insufflator 201 includes a heater base 204 and humidifier chamber 203, with the chamber 203 in use in contact with the heater base 204 so that the heater base provides heat to the chamber. The insufflation gases are passed through the chamber 203 so that they become humidified to an appropriate level of moisture. The system includes a delivery conduit that connects between the humidification chamber 203 and the peritoneal cavity or surgical site. The conduit has a first end and second end, the first end being connected to the outlet of the humidification chamber 203 and receiving humidified gases from the chamber 203. The second end of the conduit is placed in the surgical site or peritoneal cavity and humidified insufflation gases travel from the chamber 203, through the conduit and into the surgical site to insufflate and expand the surgical site or peritoneal cavity. The system also includes a controller (not shown) that regulates the amount of humidity supplied to the gases by controlling the power supplied to the heater base 204.

The smoke evacuation system 202 comprises a discharge or exhaust limb 205, a discharge assembly 207 and a filter 206. The discharge limb 205 connects between the filter 206 and the discharge assembly 207, which in use is located in or adjacent to the operative site. The discharge limb 205 is a self-supporting conduit or tube (the conduit is capable of supporting its own weight without collapsing) with two open ends: an operative site end and an outlet end is made of a breathable foamed material as described in this specification.

When saturated gases pass out of the abdominal cavity, they contact the cooler walls of the discharge limb, which is normally around one meter in length or thereabouts and moisture in the gases tends to condense onto the walls of the discharge limb or exhaust conduit. Water vapour can also condense on the filter, which can saturate the filter and cause it to become blocked. This potentially causes an increase in back pressure and hinders the ability of the system to clear smoke.

The present medical tubing as described above with reference to breathing tubes, is also suitable for application in the delivery limb of a surgical humidification system. In particular, the medical tubing of the present invention is appropriate for use in the evacuation or exhaust limb of a smoke evacuation system. The performance benefits of the tubing are a result of the improved rainout performance (i.e. less condensation forming) of the tubes of the present invention.

Other

It is anticipated that the present invention will find other medical applications to which it is particularly suited. Any application where consistent heating of tubing conveying a humid gas in order to reduce the formation of condensation could benefit from the low cost and efficient heating of the present invention.

The foregoing description of the inventions includes preferred forms thereof. Modifications may be made thereto without departing from the scope of the invention. The disclosures and the descriptions herein are purely illustrative and are not intended to be in any sense limiting.

What is claimed is:

1. A component comprising:

a corrugated tube wherein the corrugation profile comprises a plurality of alternating outer crests and inner troughs, each of the plurality of outer crests including local troughs comprising an inward dip, wherein the corrugated tube is a medical tube configured to provide a pathway between components of a medical circuit, wherein the corrugated tube transitions from a helical corrugation profile to an annular corrugation profile, and wherein the annular corrugation profile includes angled channels to allow the first heater wire and second heater wire to step over each of the annular rings of the annular corrugation profile;

a first heater wire associated with at least one inward dip of the plurality of outer crests; and a second heater wire associated with at least one of the plurality of inner troughs.

2. The component of claim 1, wherein the first and second heater wires have different heating densities.

3. The component of claim 1 further comprising a sheath that covers the component and the first and second heater wires, the sheath configured to retain the first and second heater wires.

4. The component of claim 3, wherein the sheath is configured to trap air within the plurality of inner troughs and the inward dips.

5. The component of claim 3, wherein the sheath is bonded to the corrugated tube at least one of the plurality outer crests.

6. The component of claim 1 further comprising a sensor wire that is associated with at least one inward dip of the plurality of crests or at least one of the plurality of inner troughs.

7. The component of claim 6, wherein the sensor wire is associated with the same inward dip as the first heater wire.

8. The component of claim 6, wherein the sensor wire is associated with a different inward dip than the first heater wire.

9. The component of claim 6, wherein the sensor wire is associated with the same inner trough as the second heater wire.

10. The component of claim 6, wherein the sensor wire is associated with a different inner trough than the second heater wire.

11. The component of claim 1, wherein at least one of the first heater wire or the second heater wire is also a sensor wire.

12. The component of claim 1, wherein the corrugated tube comprises a wall with uniform thickness.

13. The component of claim 1, wherein the corrugated tube comprises a wall with variable thickness, the wall comprising a maximum thickness and a minimum thickness wherein the maximum thickness is no more than three times the minimum thickness.

14. The component of claim 1, wherein each of the plurality of outer crests comprise a maximum outer and inner radius of the corrugated tube and each of the plurality of inner troughs comprise a minimum inner and outer radius of the corrugated tube.

15. The component of claim 1, wherein the corrugated tube is formed in a helical manner.

16. The component of claim 15, wherein the corrugated tube comprises a plurality of helical corrugations.

17. The component of claim 15, wherein a helix of the helical corrugated tube comprises a varying pitch along the length of the corrugated tube.

* * * * *

UNITED STATES PATENT AND TRADEMARK OFFICE

CERTIFICATE OF CORRECTION

PATENT NO. : 9,872,967 B2
APPLICATION NO. : 15/265735
DATED : January 23, 2018
INVENTOR(S) : David John Sims It is certified that error appears in the above-identified patent and that said Letters Patent is hereby corrected as shown below:

In Column 1 at Line 26, Change "in," to --in--.

In Column 4 at Line 15, Change "said," to --said--.

In Column 4 at Line 45, Change "en vises" to --comprises--.

In Column 5 at Line 15, Change "of," to --of--.

In Column 9 at Line 24, Change "my," to --any,--.

In Column 14 at Line 1, Change "saturation," to --saturation--.

In Column 14 at Line 10 (approx.), Change "Asumptions" to --Assumptions--.

In Column 15 at Line 46, Change "in," to --in--.

In Column 15 at Line 49, Change "in," to --in--.

In Column 16 at Line 32, Change "limb" to --limb.--.

In Column 18 at Line 16, In Claim 5, change "at" to --at at--.

Signed and Sealed this
First Day of May, 2018

Andrei Iancu
*Director of the United States Patent and Trademark Office*